United States Patent [19]

Zaby et al.

[11] Patent Number: 5,739,258
[45] Date of Patent: Apr. 14, 1998

[54] PROCESS FOR PREPARING DIARYL CARBONATES AND THE POLYCARBONATES OBTAINABLE THEREFROM

[75] Inventors: Gottfried Zaby, Leverkusen; Hans-Josef Buysch, Krefeld; Steffen Kühling, Meerbusch; Carsten Hesse, Krefeld; Johann Rechner, Kemper, all of Germany

[73] Assignee: Bayer AG, Leverkusen, Germany

[21] Appl. No.: 804,287

[22] Filed: Mar. 3, 1997

[30] Foreign Application Priority Data

Mar. 8, 1996 [GB] United Kingdom ............... 19609057

[51] Int. Cl.$^6$ .................................................. C08G 64/00
[52] U.S. Cl. ............................................ 528/198; 528/196
[58] Field of Search ............................... 528/196, 198

[56] References Cited

U.S. PATENT DOCUMENTS

| | | | |
|---|---|---|---|
| 4,096,169 | 6/1978 | Chalk | 528/196 |
| 4,187,242 | 2/1980 | Chalk | 528/196 |
| 4,465,721 | 8/1984 | McAlister | 528/86 |
| 4,954,613 | 9/1990 | Hudson | 528/371 |
| 5,189,139 | 2/1993 | Tuinstra et al. | 528/196 |
| 5,276,134 | 1/1994 | Tuinstra et al. | 528/371 |
| 5,336,750 | 8/1994 | Tuinstra et al. | 528/196 |
| 5,502,232 | 3/1996 | Buysch et al. | 558/270 |

FOREIGN PATENT DOCUMENTS

| | | |
|---|---|---|
| 0 583 935 | 2/1994 | European Pat. Off. . |
| 0 583 937 | 2/1994 | European Pat. Off. . |
| 0 583 938 | 2/1994 | European Pat. Off. . |
| 0 654 461 | 5/1995 | European Pat. Off. . |
| 27 38 437 | 4/1978 | Germany . |
| 88 569 | 4/1995 | Luxembourg . |
| WO 93/03000 | 2/1993 | WIPO . |

OTHER PUBLICATIONS

Orbit Abstract of DE 27 38 437 (Apr. 13, 1978).
Abstract of JP04257546–A, Asahi Chem.Ind.Co.Ltd. Feb. 7, 1991, 91JP–016450, E: General Chemistry, Week 9243.
Abstract of JO 1165–551–A, Asahi Chem.Ind.K.K, Dec. 22, 1987, JP–322910,E: General Chemistry, Week 8932.
Obit Abstract of EP 0 654 461 (May 24, 1995).
Orbit Abstract of LU 88 569 (Apr. 5, 1995).

*Primary Examiner*—Terressa Mosley
*Attorney, Agent, or Firm*—Connolly & Hutz

[57] ABSTRACT

The invention relates to a process for preparing a diaryl carbonate by oxidative carbonylation of the basic aromatic hydroxy compound, in which the aromatic hydroxy compound is the one which is eliminated during melt polycondensation of this diaryl carbonate with a bisphenol. Accordingly the invention also relates to the preparation of polycarbonates by melt polycondensation of diaryl carbonates with bisphenols in which the aromatic hydroxy compounds which is eliminated is used again to prepare the diaryl carbonate. In the event that the aromatic hydroxy compound eliminated is also the basic unit in the bisphenol used, proportions of it may be used to prepare both the diaryl carbonate and the bisphenol.

15 Claims, 1 Drawing Sheet

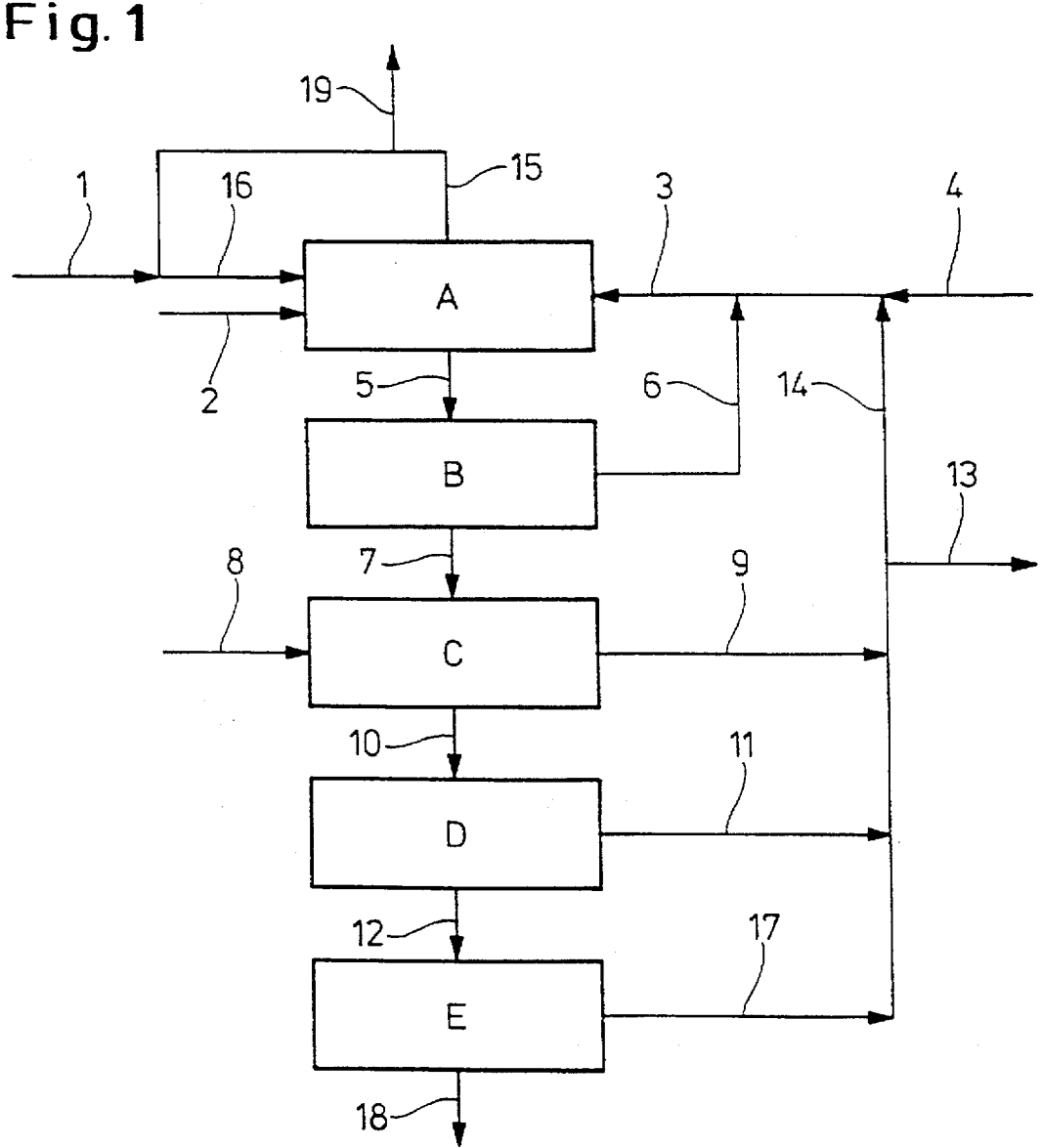

PROCESS FOR PREPARING DIARYL CARBONATES AND THE POLYCARBONATES OBTAINABLE THEREFROM

The present invention provides a materially closed and energy-coupled, phosgene-free general method for preparing diaryl carbonates and solvent-free polycarbonates, starting from bisphenols and diaryl carbonates, characterised in that the monophenol, which is released during transesterification to give the oligo/polycarbonate, is re-used in the phosgene-free preparation of diaryl carbonates by oxidative carbonylation of the corresponding monophenol.

It is known that aromatic carbonates can be prepared by oxidative reaction of an aromatic hydroxy compound with carbon monoxide in the presence of a noble metal catalyst (DE-OS 2 738 437, JP-01 165 551, WO 93/03000, EP 583 935, EP 583 937 and EP 583 938). Palladium is preferably used as the noble metal. In addition, a co-catalyst (e.g. manganese or cobalt salts), a base, a quaternary salt, a variety of quinones or hydroquinones and drying agents may be used. The reaction may be performed in a solvent, preferably methylene chloride.

When reacting aromatic hydroxy compounds with carbon monoxide and oxygen, one mole of water is released per mole of organic carbonate formed, which hinders progress of the reaction. The use of molecular sieves to absorb the reaction water, for instance in accordance with DE-OS 27 38 437, makes industrial application of the process unattractive, because large amounts of molecular sieve (100–500% excess) are required for effective separation of the water from the liquid phase, which then has to be regenerated in a highly complex manner. The space-time yields obtainable by this method are too low for industrial application. A large-scale continuous method of performing the reaction has not been disclosed.

JP-04 257 546 describes a process in which organic carbonates are prepared by oxidative reaction of an aromatic hydroxy compound with carbon monoxide in the presence of a noble metal catalyst and a quaternary salt by continuously feeding to a distillation column at 150°–205° C. and 30–50 bar. The water of reaction is continuously distilled off. The disadvantage of this process is that in order to remove the water of reaction, a distillation column has to be used which, due to its structure, permits only short residence times. The space-time yields which can be achieved with this process are therefore, at only 17.8 g/l h, very low. Performing the reaction in a distillation column is associated with the use of large amounts of halides at high temperatures (150°–205° C.). This produces considerable corrosion problems which also result in high equipment costs. In addition, a person skilled in the art knows that the iodide which is preferably used as a quaternary salt is not stable under the stated reaction conditions and is largely oxidised to iodine. This leads to large losses of quaternary salt and to the formation of secondary products, which greatly impairs selectivity and thus the economic viability of this process. In addition at these high temperatures and pressures, rapid deactivation of the homogeneous catalyst system, caused by the halogen losses and particle growth of the palladium, are to be expected so that economic application of this process is not possible.

Furthermore, all the processes known from the prior art use fresh, non-recycled monohydroxy compounds. Material coupling to a melt polycarbonate plant has not hitherto been disclosed and seems to be impossible from the disclosures in the prior art. Furthermore, completely phosgene-free preparation of aromatic polycarbonates by the transesterification of diaryl carbonates from oxidative carbonylation of aromatic hydroxy compounds with bisphenols has not hitherto been described. There is therefore the object of finding a process which permits the preparation of diaryl carbonates by oxidative carbonylation to be performed with high space-time yields and with material coupling to a melt polycarbonate plant.

Surprisingly, it has now been found that oxidative carbonylation of the aromatic monohydroxy compound can be performed with high space-time yields and a selectivity, with respect to the monohydroxy compound, of greater than 99%, if the return stream from a melt polycarbonate plant is used as the monohydroxy compound. This was surprising because the recycled monohydroxy compound, as compared with a fresh monohydroxy compound, may be contaminated and this type of contamination can greatly impair both the selectivity and the rate of reaction of oxidative carbonylation and rapid deactivation of the catalyst system was feared. In the event, a general process for diaryl carbonates and the polycarbonates obtainable therefrom by melt condensation is produced.

The general process according to the invention is flexible, simple to perform and provides products in high purity, which is extremely important for the overall process, and thus includes the following process steps (see FIG. 1):

1. preparation of the diaryl carbonate by oxidative carbonylation of the basic aromatic hydroxy compound,
2. separation from the preparation mixture and purification of the diaryl carbonate,
3. transesterification of the diaryl carbonate with an aromatic dihydroxy compound to give an oligo/polycarbonate and release the aromatic monohydroxy compound,
4. isolation or separation of the polycarbonate and the aromatic monohydroxy compound,
5. return of the aromatic monohydroxy compound to the preparation of diaryl carbonate step.

Accordingly, the invention relates to a process for preparing a diaryl carbonate of the formula (I)

$$R^1-O-CO-O-R^1 \qquad (I)$$

by reacting the basic aromatic hydroxy compound of the formula (II)

$$R^1-OH \qquad (II)$$

wherein, in the formulae

R$^1$ represents phenyl, methylphenyl, ethylphenyl or chlorophenyl, with carbon monoxide and oxygen in the presence of a platinum metal catalyst, a co-catalyst, a quaternary salt and a base, which is characterised in that the aromatic hydroxy compounds used are those which are eliminated during the melt polycondensation of (I) with a bisphenol of the formula

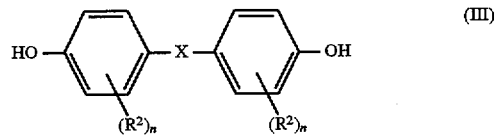

in which

X represents a single bond, —S—, —SO$_2$—, —CO—, —O—, C$_1$–C$_8$—alkylidenes or C$_5$–C$_9$-cycloalkylidenes, R$^2$ represents methyl, Cl or Br and n represents the numbers 0, 1 or 2.

The invention also provides a process for preparing polycarbonates by melt polycondensation of a diaryl carbonate with a bisphenol, with elimination of the basic aromatic hydroxy compound in the diaryl carbonate, characterised by the steps a) preparation of a diaryl carbonate of the formula

$$R^1\text{—O—CO—O—}R^1 \quad\quad (I)$$

by oxidative carbonylation of the basic aromatic hydroxy compound of the formula

$$R^1\text{—OH} \quad\quad (II)$$

wherein, in the formulae

R$^1$ represents phenyl, methylphenyl, ethylphenyl or chlorophenyl, with carbon monoxide and oxygen in the presence of a platinum metal catalyst, a co-catalyst, a quaternary salt and a base, b) separation and purification of the diaryl carbonate, c) transesterification of the diaryl carbonate with a bisphenol of the formula

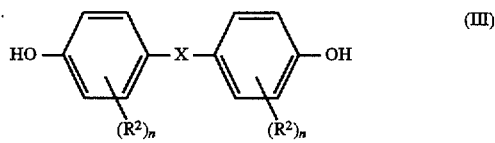

in which

X represents a single bond, —S—, —SO$_2$—, —CO—, —O—, C$_1$–C$_8$-alkylidenes or C$_5$–C$_9$-cycloalkylidenes, R$^2$ represents methyl, Cl or Br and n represents the numbers 0, 1 or 2, in a melt polycondensation process with formation of the corresponding oligo or polycarbonate and elimination of the aromatic hydroxy compound (II), d) separation of the aromatic hydroxy compound (II) from the oligo or polycarbonate and e) return of (II) to step a).

Bisphenols which can be used according to the invention are, for instance: 4,4'-dihydroxydiphenyl, 4,4'-dihydroxydiphenyl sulphide, 2,2-bis-(4-hydroxyphenyl) propane (bis-phenol A), 2,2-bis-(3,5-dimethyl-4-hydroxyphenyl)-propane, 2,2-bis-(3,5-dichloro-4-hydroxyphenyl)-propane, 2,2-bis-(3,5-dibromo-4-hydroxyphenyl)propane, 1,1-bis-(4-hydroxyphenyl)-cyclohexane, 1,1-bis-(4-hydroxyphenyl)-3,3,5-trimethylcyclohexane (with C$_9$-alkylidenes), bis-(4-hydroxyphenyl)-sulphone and 4,4'-dihydroxybenzophenone.

Preferred bisphenols are those of the formula

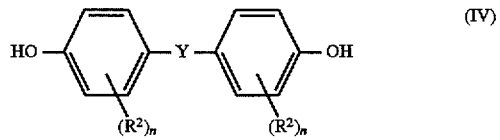

in which

Y represents a single bond, —O—, C$_1$–C$_5$-alkylidenes or C$_6$–C$_9$-cycloalkylidenes and R$^2$ and n are defined as above.

Particularly preferred bisphenols, from those mentioned above, are 2,2-bis-(4-hydroxyphenyl)-propane and 1,1-bis-(4-hydroxyphenyl)-3,3,5-trimethylcyclohexane, specifically 2,2-bis-(4-hydroxyphenyl)-propane.

Hydroxy compounds (II) which can be used according to the invention, which are the basic units in the diaryl carbonates (I), are for example: phenol, o-, m-, p-cresol, o-, m-, p-ethylphenol and o-, m-, p-chlorophenol, preferably phenol and o-, m-, p-cresol, in particular phenol.

Preferred diaryl carbonates are diesters of phenol or alkyl-substituted phenols, e.g. diphenyl carbonate, or e.g. dicresyl carbonate, in particular diphenyl carbonate (DPC).

Preparation of the diaryl carbonates by oxidative carbonylation is preferably performed in a known manner using a catalyst system consisting of a base, a quaternary salt, a platinum metal or a platinum metal compound and a co-catalyst.

Bases which can be used to synthesise diaryl carbonates according to the invention are tertiary amines such as, for example, trimethylamine, triethylamine, tripropylamine, tributylamine, tripentylamine, alkali metal hydroxy compounds such as lithium hydroxide, sodium hydroxide, potassium hydroxide, rubidium hydroxide and caesium hydroxide, alkali metal salts of aromatic hydroxy compounds of the formula (II), in which R$^1$ is defined in the same way as given above. An alkali metal salt of the aromatic hydroxy compound (II) which it is intended be convert into organic carbonate (I), is specifically preferred. These alkali metal salts may be lithium, sodium, potassium, rubidium or caesium salts. Lithium, sodium and potassium phenolates are preferably used, in particular sodium phenolate. The alkali metal phenolate may be added to the reaction mixture as a pure compound in the solid form or as a melt. Obviously, the hydrates of the alkali metal phenolates may also be used in the process according to the invention. An example of such a hydrate which may be mentioned here, without restricting the process according to the invention, is sodium phenolate trihydrate. The amount of added water, however, is preferably adjusted so that at most 5 moles of water are used per mole of base. Higher amounts of water generally lead to poor conversions and decomposition of the carbonate produced. In a further embodiment of the invention, the alkali metal phenolate is added to the reaction mixture as a solution which contains 0.1 to 80 wt. %, preferably 0.5 to 65 wt. %, in particular 1–50 wt. % of alkali metal phenolate. Either alcohols or phenols, such as for example the phenol being converted, or else inert solvents may be used as solvent. Those mentioned below as suitable for reaction media may be mentioned. These solvents may be used on their own or in any combination with each other. Thus, in one embodiment of the process according to the invention, for example, the base is dissolved in a phenol melt which has been diluted with an inert solvent. Preferably, the base is dissolved in the melt of an aromatic hydroxy compound. In particular, the base is dissolved in a melt of the aromatic hydroxy compound which it is intended to convert into an organic carbonate. Specifically, the base is added dissolved in phenol. The base is added in an amount which does not depend on the stoichiometry. The ratio of platinum metal, for example palladium, to base is preferably selected so that 0.1 to 5000, preferably 3 to 2000, in particular 9 to 1000 equivalents of base are added per gram atom of platinum metal, for example palladium. The platinum metal is calculated as metal here, but may nevertheless be present in the metallic or bonded form in various oxidation states.

The process for diaryl carbonate preparation according to the invention is preferably performed without a solvent. Obviously, inert solvents may also be used. Examples of solvents which may be mentioned are dimethylacetamide, N-methypyrrolidone, dioxane, t-butanol, cumyl alcohol, isoamyl alcohol, tetramethylurea, diethylene glycol, halogenated hydrocarbons, such as chlorobenzene or dichlorobenzene, and ethers.

Platinum metal catalysts which are suitable for the preparation of diaryl carbonates according to the invention consist of at least one metal from group VIII (CAS nomenclature), preferably palladium. It may be used in the process according to the invention in a variety of forms. Palladium may be used in the metallic form or preferably in the form of palladium compounds in oxidations states 0 and +2, such as, for example, palladium(II) acetylacetonate, halides, carboxylates of $C_2$–$C_6$-carboxylic acids, nitrate or oxides, or palladium complexes which can contain, for example, carbon monoxide, olefins, amines, phosphines and halides. Palladium bromide and palladium acetylacetonate are particularly preferred.

The amount of platinum metal catalyst is not restricted in the process according to the invention. Preferably, enough catalyst is used for the concentration of metal in the reaction mixture to be 1–3000 ppm, concentrations of 5–500 ppm are particularly preferred.

The co-catalyst for the process according to the invention is a metal from groups IIIB, IVB, VB, IB, IIB, VIB or VIIB of the periodic system of elements (CAS nomenclature) or the iron group, in the form of a compound, wherein the metal may be used in different oxidation states. Without restricting the process according to the invention, compounds of manganese(II), manganese(III), copper(I), copper(II), cobalt (II), cobalt(III), vanadium(III) and vanadium(IV) may be mentioned. The metals may be used, for example, as halides, oxides, carboxylates of $C_2$–$C_6$-carboxylic acids, diketonates or nitrates as well as complex compounds which may contain, for example, carbon monoxide, olefins, amines, phosphines and halides. Manganese compounds are preferably used in the process according to the invention, in particular manganese(II) compounds or complexes, specifically manganese(II) acetylacetonate.

The co-catalyst is used in an amount such that its concentration is in the range 0.0001 to 20 wt. % of the reaction mixture, the concentration range being preferably 0.005 to 5 wt. %, in particular 0.01 to 2 wt. %.

The quaternary salts used in the context of the invention may be, for example, ammonium, phosphonium or sulphonium salts substituted with organic groups. Ammonium, phosphonium and sulphonium salts which have $C_6$–$C_{10}$-aryl, $C_7$–$C_{12}$-aralkyl and/or $C_1$–$C_{20}$-alkyl groups as organic groups and a halide, tetrafluoroborate or hexafluorophosphate as anion are suitable for use in the process according to the invention. The organic groups in the quaternary salts may be of the same or different types from among the groups mentioned. Ammonium salts which have $C_6$–$C_{10}$-aryl, $C_7$–$C_{12}$-aralkyl and/or $C_1$–$C_{10}$-alkyl groups and a halide as anion are preferably used in the process according to the invention, in particular tetrabutylammonium bromide. The amount of this type of quaternary salt may be, for example, 0.1–20 wt. %, with respect to the weight of the reaction mixture. This amount is preferably 0.5–15 wt. %, in particular 1–5 wt. %.

The process according to the invention is preferably performed without a solvent, at 30° to 200° C, preferably at 30° to 150° C., in particular at 40° to 120° C. and at a pressure of 1 to 200 bar, preferably 2 to 100 bar, in particular 5 to 50 bar.

The composition of the reaction gases carbon monoxide and oxygen may be varied between wide concentration limits, but it is expedient to use a $CO:O_2$ ratio (standardised to CO) of 1:(0.001–1.0), preferably 1:(0.01–0.5) and in particular of 1:(0.02–0.3). The oxygen partial pressure is sufficiently large, with these molar ratios, to be able to achieve high space-time yields and at the same time not to form explosive carbon monoxide/oxygen gas mixtures. The reaction gases are not subject to particular purity requirements, so synthesis gas can be used as a source of CO and air as an $O_2$ carrier, but care must be taken to ensure that no catalyst poisons such as, for example sulphur or its compounds, are introduced. In a preferred embodiment of the process according to the invention, pure CO and pure oxygen are used.

In the process according to the invention, the water contained in the reactants and the water being continuously produced during reaction are stripped out with excess reaction gas. The reaction gas, consisting of carbon monoxide, oxygen and an inert gas such as nitrogen, methane, neon or argon, preferably nitrogen, is introduced in an amount of 1–100 000 Nl per liter of reaction solution, preferably 5–50 000 Nl per liter of reaction solution and in particular 10–10 000 Nl per liter of reaction solution, per hour.

10 to 100%, preferably 15 to 100%, in particular 20 to 100% of the amount of aromatic hydroxy compound present as return stream from the polycarbonate plant is supplied to the diaryl carbonate reactor. In a further embodiment, the remaining amounts of aromatic hydroxy compound from melt polycarbonate preparation, that is 90 to 0%, preferably 85 to 0%, in particular 80 to 0%, and only in the event that the aromatic hydroxy compound eliminated is also the basic unit in the bisphenol, is also used in the preparation of the bisphenol, wherein the limit of 0% (zero) indicates the case in which no aromatic hydroxy compound from the return stream from the polycarbonate plant is used to prepare the bisphenol.

In an idealised form, these relationships may be shown as follows, using bisphenol A poly/oligocarbonate as an example:

(1)
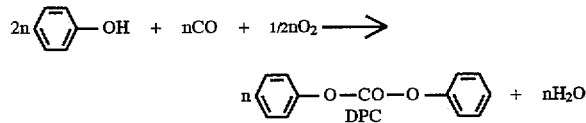

(2)
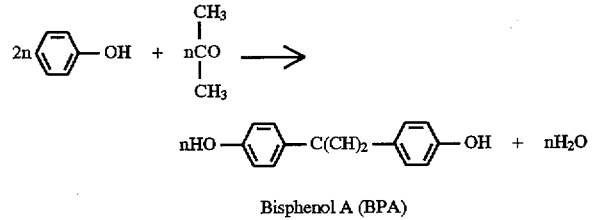

Bisphenol A (BPA)

(3)
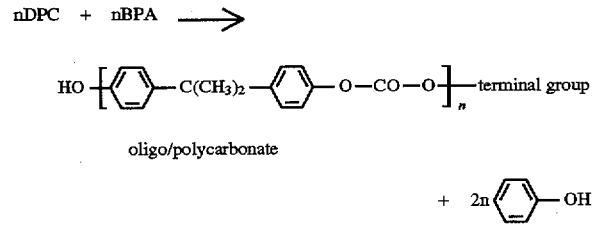

oligo/polycarbonate

Of the 4n moles of phenol used in equations (1) and (2), therefore, 2n moles are eliminated again in melt polycondensation, according to equation (3), and may be returned to equations (1) and (2).

Isolation and purification of the diaryl carbonate prepared by the process according to the invention may be performed in accordance with the known prior art, by distillation, extraction and/or crystallisation.

The diaryl carbonate prepared in this way is now used directly for transesterification (melt polycondensation) with an aromatic dihydroxy compound (bisphenol). With respect to 1 mole of bisphenol, the diaryl carbonates are used in an amount of 1.01 to 1.30 moles, preferably 1.02 to 1.15 moles. The degree of polycondensation, and thus the molecular weight, is adjusted via the molar ratio. Thus oligocarbonates or thermoplastic polycarbonates are obtained using the molar masses given above. Preparation of polycarbonates may take place in one step or, via oligocarbonates, in 2–4 steps. Oligocarbonates are readily storable precursors of polycarbonates.

The polycarbonates may be branched in a predictable and controlled manner by the use of small amounts of branching agents. Suitable branching agents are: phloroglucine, 4,6-dimethyl-2,4,6-tri-(4-hydroxyphenyl)-heptene-2,4,6-dimethyl-2,4,6-tri(4-hydroxyphenyl)-heptane, 1,3,5-tri-(4-hydroxyphenyl)-benzene, 1,1,1-tri-(4-hydroxyphenyl)-ethane, tri-(4-hydroxyphenyl)-phenylmethane, 2,2-bis-[4,4-bis-(4-hydroxyphenyl)-cyclohexyl]-propane, 2,4-bis-(4-hydroxyphenyl-isopropyl)-phenol, 2,6-bis-(2-hydroxy-5'-methylbenzene)-4-methylphenol, 2-(4-hydroxyphenyl)-2-(2,4-dihydroxyphenyl)-propane, hexa-(4-(4-hydroxyphenyl-isopropyl)-phenyl)orthoterephthalate, tetra-(4-hydroxyphenyl)-methane, tetra-(4-(4-hydroxyphenyl-isopropyl)-phenoxy)-methane, 1,4bis-(4',4"-dihydroxytriphenyl)-methyl)benzene and in particular a,a', a"-tris-(4-hydroxyphenyl)-1,3,5-triisopropylbenzene. Further possible branching agents are 2,4-dihydroxybenzoic acid, trimesic acid, cyanuric chloride and 3,3-bis-(3-methyl-4-hydroxyphenyl)-2-oxo-2,3-dihydroindole. The optionally incorporated mounts of 0.05 to 2 mol-% of branching agents, with respect to the bisphenols used, may be added together with the bisphenols.

It is advantageous if the reaction components for the preparation of oligocarbonates or for the first step in a multi-step preparation of polycarbonates, that is the bisphenols and diaryl carbonates, do not contain any alkali or alkaline earth metal ions, wherein amounts of less than 0.1 ppm of alkali and alkaline earth metal ions may be tolerated. These types of pure bisphenols and diaryl carbonates are obtainable, for example, by recrystallising, washing or distilling these substances. According to the invention, the concentration of alkali and alkaline earth metal ions in both the bisphenol and also the diaryl carbonate should be less than 0.1 ppm.

The transesterification reaction of bisphenol and diaryl carbonate in the melt is preferably performed in two steps. In the first step, melting of the bisphenol and diaryl carbonate at temperatures of 80°–250° C., preferably 100°–230° C., in particular 120°–190° C. takes place under atmospheric pressure over 0.01–5 hours, preferably 0.25–3 hours. After adding a catalyst, a vacuum is applied (down to less than 2 mm Hg) and the temperature is increased (up to 260° C.) by distilling off the aromatic hydroxy compound (II), the oligocarbonate is prepared from the bisphenol and the diaryl carbonate. The oligocarbonate prepared in this way has an average molecular weight $\overline{M}_w$ (determined by measuring the rel. solution viscosity in dichloromethane or in mixtures of equal amounts by weight of phenol and o-dichlorobenzene, calibrated by light scattering) in the range 2000 to 18 000, preferably 4 000 to 15 000. The major proportion (>80%) of aromatic hydroxy compound (II), which is the basic unit in the diaryl carbonate (I), is recovered, within the scope of the range mentioned above, and returned to the process for fresh preparation of diaryl carbonate.

In the second step, the polycarbonate is prepared during melt polycondensation by further increasing the temperature to 250°–320° C., preferably 270°–295° C., at a pressure of <2 mm Hg. Here, the remainder of the aromatic hydroxy compound (II), which is the basic unit in the diaryl carbonate (I), is recovered. There are small losses of (II) of about <5%, preferably <2%, in particular <1%, caused by terminal groups in the polycarbonate and residues of (II) in the polycarbonate. These losses have to be compensated for with corresponding amounts of (II) for preparing the diaryl carbonate. To suppress accumulation of contaminants, a purge stream can be withdrawn from the recycled (II) before it is used again to prepare the diaryl carbonate.

Catalysts for the transesterification of a diaryl carbonate with a bisphenol according to the invention are any inorganic or organic basic compounds, for example: lithium, sodium, potassium, caesium, calcium, barium, magnesium, hydroxides, carbonates, halides, phenolates, diphenolates, fluorides, acetates, phosphates, hydrogen phosphates or boranates, nitrogen and phosphorus bases such as, for example, tetramethylammonium hydroxide, tetramethylammonium acetate, tetramethylammonium fluoride, tetramethylammonium tetraphenylboranate, tetraphenylphosphonium fluoride, tetraphenylphosphonium tetraphenylboranate, dimethyldiphenylammonium hydroxide, tetraethylammonium hydroxide, DBU (diazabicycloundecane), DBN (diaza-bicyclononane) or guanidine systems such as, for example, 1,5,7-triazabicyclo-[4,4,0]-dec-5-ene, 7-phenyl-1,5,7-triazabicyclo-[4,4,0]-dec-5-ene, 7-methyl- 1,5,7-triazabicyclo-4,4,0]-dec-5-ene, 7,7'-hexylidene-di-1,5,7-triazabicyclo-[4,4,0]-dec-5-ene, 7,7'-decylidene-di-1,5,7-triazabicyclo-[4,4,0]-dec-5-ene or 7,7'-dodecylidene-di-1,5,7-triazabicyclo-[4,4,0]-dec-5-ene or phosphazenes such as, for example, phosphazene base $P_1$-t-oct=tert.-octyl-imino-tris-(dimethylamino)-phosphorane, phosphazene base $P_1$-t-butyl=tert.-butyl-imino-tris-(dimethylamino)-phosphorane or BEMP=2-tert.-butylimino-2-diethylamino-1,3-dimethyl-perhydro-1,3-diaza-2-phosphorine.

These catalysts are used in amounts of $10^{-2}$ to $10^{-8}$ moles per mole of bisphenol. The catalysts may also be used in combination (two or more) with each other.

When using alkali/alkaline earth metal catalysts it may be advantageous to add them at a later time (e.g. after synthesis of the oligocarbonate, during polycondensation, in the second step). Addition of alkali/alkaline earth metal catalysts can take place e.g. as a solid or as a solution in water, phenol, oligocarbonate or polycarbonate. The use of alkali or alkaline earth metal catalysts does not conflict with the previously mentioned requirement about purity of the reaction partners.

Reaction of bisphenol and diaryl carbonate to give polycarbonate in the context of the invention may be performed batchwise or continuously, for example in stirred tanks, thin-layer evaporators, falling film evaporators, stirred tank cascades, extruders, kneaders, simple disc reactors and high-viscosity disc reactors.

Aromatic polycarbonates from the process according to the invention have average weight molecular weights $\overline{M}_w$ of 18 000 to 80 000, preferably 19 000–50 000, determined by measuring the rel. solution viscosity in dichloromethane or in mixtures of equal amounts by weight of phenol and o-dichlorobenzene, calibrated by light scattering.

The crude (II) which is isolated during the transesterification process may, depending on the transesterification conditions and distillation conditions, be contaminated, inter alia, with diaryl carbonate, bisphenol, salicylic acid, phenyl salicylate, isopropenylphenol, phenyl phenoxybenzoate, xanthone or the hydroxymonoaryl carbonate. Purification is not necessarily required, but may take place using conventional methods of purification, that is for example distillation or recrystallisation. The purity of (II) is then >97%, preferably >98%, in particular >99%, and is then sufficiently pure to be recycled in accordance with the invention to prepare the diaryl carbonate.

EXAMPLE

The attached FIG. 1 shows a block diagram of the flexible pilot plant used to perform the process according to the invention for preparing a diaryl carbonate and the process according to the invention for preparing polycarbonates. The equipment shown in FIG. 1 consists of reactor A for preparing diphenyl carbonate (DPC), device B for separating the DPC from the crude reaction mixture flowing out of A, wherein ongoing purification of the DPC may optionally also be performed in B, transesterification reactors C and D for the first and second steps of oligomerisation and transesterification reactor E for melt polycondensation in the event that the process is performed in several steps, here for example as the third step.

Carbon monoxide and oxygen were metered into reactor A through the pipes (1) and (2) respectively (molar ratio $CO:O_2$ (standardised to CO) 1:0.035) as the feed gas. With this molar ratio, the partial pressure of oxygen is large enough to be able to achieve a high space-time yield of about 150 g DPC/l·h while at the same time it is not possible for an explosive carbon monoxide/oxygen gas mixture to be produced. The optimum oxygen concentration is ensured by supplying the carbon monoxide and oxygen separately.

Phenol was introduced to reactor A via pipe (3), whereas supplementary phenol and catalyst system were fed through pipe (4). The temperature in reactor A was 80° C. at an overall pressure of 10 bar (abs.). The water formed during reaction was stripped out via vent gas pipe (15) using excess feed gas and separated from the feed gas. The excess feed gas, after withdrawing a purge stream (pipe 19) to separate inert gases and carbon dioxide, was returned to reactor A through pipe (16).

The crude reaction mixture, containing diphenyl carbonate, was continuously withdrawn from reactor A via pipe (5) and fed to device B, where separation and purification of the DPC formed was performed. The mother liquor, containing the catalyst system, was retuned to reactor A via pipe (6). DPC recovered in B was fed to the first step of transesterification/melt polycondensation C via pipe (7). Furthermore, a stream of 2,2-bis-(4-hydroxyphenyl)-propane (bisphenol A) was fed to C via pipe (8).

The reaction in C and D took place in the presence of $10^{-6}$ moles of tetraphenylphosphonium tetraphenylboranate per mole of bisphenol A converted as a transesterification catalyst, first at a temperature of 180° C., which was increased to 220° C., wherein the pressure was simultaneously reduced to 100 mbar. The eliminated phenol was returned to reactor A via pipe (9), the oligocarbonate was fed to the second step of transesterification/melt polycondensation D via pipe (10). More phenol was eliminated in D at a temperature of 250° C. and a pressure of 5 mbar and returned to reactor A via pipe (11). An oligocarbonate with a molecular weight of about 5 000 g/mol was withdrawn from transesterification reactor D via pipe (12) and fed to the third step (polycondensation reactor E). In E, the last remnants of phenol were eliminated at a temperature of 290° C. and a pressure of 0.1 mbar in the presence of $10^{-6}$ moles of NaOH per mole of bisphenol A converted and returned to reactor A via pipe (17) and manifold (14), together with the phenol eliminated in C and D, after withdrawal of a purge stream (13). Polycarbonate as process product (pipe 18) was withdrawn from polycondensation reactor E, this having a molecular weight of about 25 000 g/mol. The polycarbonate was pale yellow and solvent-free. The pilot plant was shut down after 21 days of continuous operation without any signs of loss in quality or a lowering in the molecular weight produced being detected.

We claim:

1. A process for preparing a diaryl carbonate of the formula (I)

$$R^1\text{—O—CO—O—}R^1 \qquad (I)$$

wherein said process includes the step of contacting in a reactor a group of materials consisting essentially of a basic aromatic hydroxy compound of the formula (II)

$$R^1\text{—OH} \qquad (II)$$

wherein, in the formulae $R^1$ represents phenyl, methylphenyl, ethylphenyl or chlorophenyl, carbon monoxide, oxygen, a platinum metal catalyst, a co-catalyst, a quaternary salt and a base, further wherein the basic aromatic hydroxy compound used is a compound which is eliminated during the melt polycondensation of (I) with a bisphenol of the formula

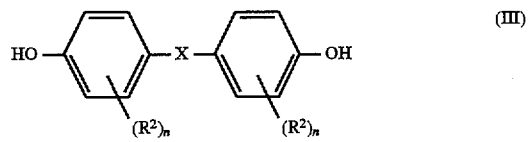

in which

X represent a single bond, —S—, —SO$_2$—, —CO—, —O—, $C_{1-C8}$-alkylidenes or $C_5$–$C_9$-cycloalkylidenes, $R^2$ represents methyl, Cl or Br and n represents the numbers 0, 1 or 2.

2. A process for preparing polycarbonates by melt polycondensation of a diaryl carbonate with a bisphenol, with elimination of a basic aromatic hydroxy compound from the diaryl carbonate, comprising the steps a) preparation of a diaryl carbonate of the formula $$R^1\text{—O—CO—O—}R^1 \qquad (I)$$

wherein said preparation includes the step of contacting in a reactor a group of materials consisting essentially of the basic aromatic hydroxy compound, which has the formula $$R^1\text{—OH} \qquad (II)$$

wherein, in the formulae $R^1$ represents phenyl, methylphenyl, ethylphenyl or chlorophenyl, carbon monoxide, oxygen, a platinum metal catalyst, a co-catalyst, a quaternary salt and a base, b) separation and purification of the diaryl carbonate, c) transesterification of the diaryl carbonate with a bisphenol of the formula

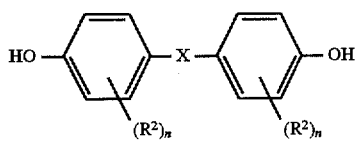

(III)

in which

X represents a single bond, —S—, —SO$_2$—, —CO—, —O—, C$_1$–C$_8$-alkylidenes or C$_5$–C$_9$-cycloalkylidenes, R$^2$ represents methyl, Cl or Br and n represents the numbers 0, 1 or 2, in a melt polycondensation process with formation of the corresponding oligo or polycarbonate and elimination of the aromatic hydroxy compound (II), d) separation of the aromatic hydroxy compound (II) from the oligo or polycarbonate and e) return of (II) to step a).

3. A process according to claim 1, characterised in that the bisphenol of formula (III) has the following structure

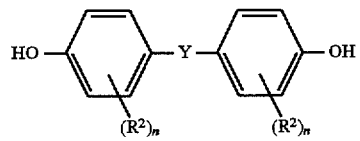

in which

Y represents a single bond, —O—, C$_1$–C$_5$-alkylidenes or C$_6$–C$_9$-cycloalkylidenes.

4. A process according to claim 1, characterised in that phenol or o-, m- or p-cresol is used as the aromatic hydroxy compound.

5. A process according to claim 1, characterised in that tertiary amines, alkali metal hydroxides or alkali metal salts of aromatic hydroxy compounds (II) are used as bases.

6. A process according to claim 1, characterised in that palladium in the metallic form or in the form of a Pd compound in oxidation state 0 or +2 is used as a platinum metal catalyst.

7. A process according to claim 1, characterised in that a metal from the groups IIIB, IVB, VB, IB, IIB, VIB, VIIB or the iron group, in the form of a compound is used as co-catalyst.

8. A process according to claim 1, characterised in that an ammonium, phosphonium or sulphonium salt substituted with organic groups is used as a quaternary salt.

9. A process according to claim 1, characterised in that 10–100% of the aromatic hydroxy compound eliminated during melt polycondensation is returned to the preparation of diaryl carbonate.

10. A process according to claim 3, wherein the bisphenol of formula (III) is 2,2-bis-(4-hydroxyphenyl)-propane or 1,1-bis-(4-hydroxyphenyl)-3,3,5-trimethyl cyclohexane.

11. A process according to claim 1, wherein the platinum metal catalyst is at least one metal from group VIII of the periodic table of the elements.

12. A process according to claim 11, wherein the platinum metal catalyst is platinum or palladium.

13. A process according to claim 1, wherein the platinum metal catalyst is a compound of palladium selected from the group consisting of palladium (II) acetylacetonate, palladium halides, palladium carboxylates of C$_2$–C$_6$-carboxylic acids, palladium nitrates and palladium oxides.

14. A process according to claim 1, wherein the platinum metal catalyst is a palladium complex which comprises at least one substance selected from the group consisting of carbon monoxide, olefins, amines, phosphines and halides.

15. A process according to claim 1, wherein the platinum metal catalyst is palladium bromide or palladium acetylacetonate.

* * * * *

UNITED STATES PATENT AND TRADEMARK OFFICE
CERTIFICATE OF CORRECTION

PATENT NO. : 5,739,258  
DATED : April 14, 1998  
INVENTOR(S) : Zaby et al.

Page 1 of 1

It is certified that error appears in the above-identified patent and that said Letters Patent is hereby corrected as shown below:

Title page,
Line 4 of section [75] Inventors: "Kemper" should be -- Kempen --.
In section [30] Foreign Application Priority Data, "[GB] United Kingdom" should read -- [DE] Germany --.

Column 10,
Line 43, $C_1-C_8$-alkylidenes" should be -- $C_1$. $C_8$- alkylidenes --.

Signed and Sealed this

Fourteenth Day of August, 2001

Attest:

NICHOLAS P. GODICI
Attesting Officer  Acting Director of the United States Patent and Trademark Office